(12) United States Patent
Filsouf

(10) Patent No.: US 7,464,430 B2
(45) Date of Patent: Dec. 16, 2008

(54) ELECTRIC TOOTHBRUSH

(76) Inventor: Ehsan Filsouf, 51-1 Northern Heights Dr., Richmond Hill, ONT (CA) L4B 4C9

( * ) Notice: Subject to any disclaimer, the term of this patent is extended or adjusted under 35 U.S.C. 154(b) by 106 days.

(21) Appl. No.: 11/322,214

(22) Filed: Jan. 3, 2006

(65) Prior Publication Data
US 2007/0151051 A1 Jul. 5, 2007

(51) Int. Cl.
*A61C 17/22* (2006.01)
(52) U.S. Cl. ............................ 15/22.1; 15/22.4; 15/23
(58) Field of Classification Search .................. 15/22.1, 15/23, 22.4
See application file for complete search history.

(56) References Cited

U.S. PATENT DOCUMENTS

| | | | | |
|---|---|---|---|---|
| 2,662,239 A | * | 12/1953 | Grover | ........................... 15/23 |
| 4,149,291 A | * | 4/1979 | Stoltz | ........................ 15/22.1 |
| 4,275,749 A | | 6/1981 | Caroli | |
| 4,882,801 A | * | 11/1989 | Benz | ............................. 15/23 |
| 4,979,387 A | * | 12/1990 | Dittmar | ...................... 73/1.45 |
| 5,794,296 A | | 8/1998 | Wong | |
| 6,047,711 A | | 4/2000 | Wagner | |
| 2005/0091773 A1 | * | 5/2005 | Gavney et al. | ................ 15/117 |

* cited by examiner

*Primary Examiner*—Shay L Karls
(74) *Attorney, Agent, or Firm*—Cantor Colburn LLP

(57) ABSTRACT

An electric toothbrush in which the brushing head moves in an elliptical motion such that, on the brushing stroke, the bristles are proximate the teeth, and in the recovery portion of the cycle the bristles are pulled away from the teeth. A position sensitive switch automatically switches from a forward to a reverse operation of the electric motor, depending on the positioning of the toothbrush in a user's hand, allowing the user to brush both the upper and lower teeth using a stroke carrying the bristles from the gum line to the ends of the teeth, as is recommended by dental professionals, without having to move the toothbrush from hand to hand or manually move the switch from the forward to the reverse positions. A bridge pad engages the face of the teeth, maintaining a proper distance between the teeth and bristles during the elliptical rotation of the brush head.

15 Claims, 10 Drawing Sheets

ELECTRIC TOOTHBRUSH

BACKGROUND OF THE INVENTION

1. Field of the Invention

The present invention relates to electric toothbrushes. More particularly, the invention comprises an electric toothbrush having a reversible, elliptical rotation pattern of the brushing head, allowing strokes which brush away from the gums, regardless of which hand the user uses or whether he is brushing the upper or lower teeth.

2. Description of the Prior Art

Electric toothbrushes are well known in the art. Most electric toothbrushes, however, provide only an up and down motion, thereby brushing into the gum on half of the brush strokes. Most of the brushes which do provide a rotary motion, and thus only brush away from the gum, as advised by dental professionals, present other problems.

U.S. Pat. No. 5,974,296, issued to Tit Shing Wong on Aug. 18, 1998, discloses an ELECTRIC TOOTHBRUSH, having a reversible, rotary brush head activated by a switch at the brush head, which is placed inside the mouth. By contrast, the switch of the present invention is contained within the handle of the toothbrush and is activated by the position of the toothbrush in the user's hand, and the brushing action of the brush head is performed with a stroking motion as opposed to a rotary motion. The present invention further includes a spacer to maintain the brush at a proper distance from the teeth during the brushing and recovery strokes, not found in Wong's brush.

Celso Caroli discloses an ELECTRICALLY DRIVEN CONTINUOUS TOOTH BRUSH in U.S. Pat. No. 4,275,479, issued on Jun. 30, 1981. A reversible, rotating brush head is controlled by a manual switch controlled by the user's fingers. By contrast, the switch of the present invention is contained within the handle of the toothbrush and is activated by the position of the toothbrush in the user's hand, and the brushing action of the brush head is performed with a stroking motion as opposed to a rotary motion. The present invention further includes a spacer to maintain the brush at a proper distance from the teeth during the brushing and recovery strokes, not found in Caroll's brush.

A METHOD AND APPARATUS FOR CONVERTING A POWER-DRIVEN TOOTHBRUSH INTO A POWER-DRIVEN FLOSSING DEVICE is disclosed in U.S. Pat. No. 6,047,711, issued to Daniel A. Wagner on Apr. 11, 2000. The toothbrush and flosser, as described do not provide elliptical rotation of the head or means of spacing the brushes away from the teeth.

None of the above inventions and patents, taken either singly or in combination, is seen to describe the instant invention as claimed.

SUMMARY OF THE INVENTION

The present invention provides an electric toothbrush which has a reversible, elliptical brushing motion which allows a user to brush from the gums to the tips of the teeth, regardless of which hand he is using or whether he is brushing the upper or lower teeth. The brush bristles are split such that they extend on either side of a soft spacer pad which may be rested against the teeth. The spacer maintains the bristles at a given distance away from the teeth, such that they brush against the teeth on the near, brushing stroke, portion of an elliptical orbit about an axis of the shaft while pulling away from the teeth on the far, recovery, portion of the elliptical orbit. An automatic, position sensitive switch allows the brush shaft to change the direction of its elliptical rotation about its axis, allowing a user to switch the brushing direction of the bristles by a simple change of the angle of the wrist in order to change from brushing the left or right or the front or the back of the teeth. A three position switch on the handle allows the user to selectively reverse the motor for brushing the upper teeth or the lower teeth.

Accordingly, it is a principal object of the invention to provide an electric toothbrush which is capable of brushing both the upper and lower teeth, with the bristles stroking away from the gums, as is recommended by dental professionals.

It is another object of the invention to provide an electric toothbrush which is able to change the direction of the bristle stroke by a simple change of wrist position.

It is a further object of the invention to provide an electric toothbrush having an spacer element to maintain the brush shaft away from the teeth, allowing the bristles to brush the teeth on the brushing portion of the cycle while preventing the shaft from hitting the teeth as it rotates about its axis.

Still another object of the invention is to provide an electric toothbrush which may, optionally, be either AC or DC operated.

An additional object of the invention is to provide an electric toothbrush which is relatively light weight, yet durable.

It is again an object of the invention to provide an electric toothbrush which is relatively economical to purchase and operate.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Various other objects, features, and attendant advantages of the present invention will become more fully appreciated as the same becomes better understood when considered in conjunction with the accompanying drawings, in which like reference characters designate the same or similar parts throughout the several views, and wherein.

DETAILED DESCRIPTION OF THE PREFERRED EMBODIMENTS

Figure 1:
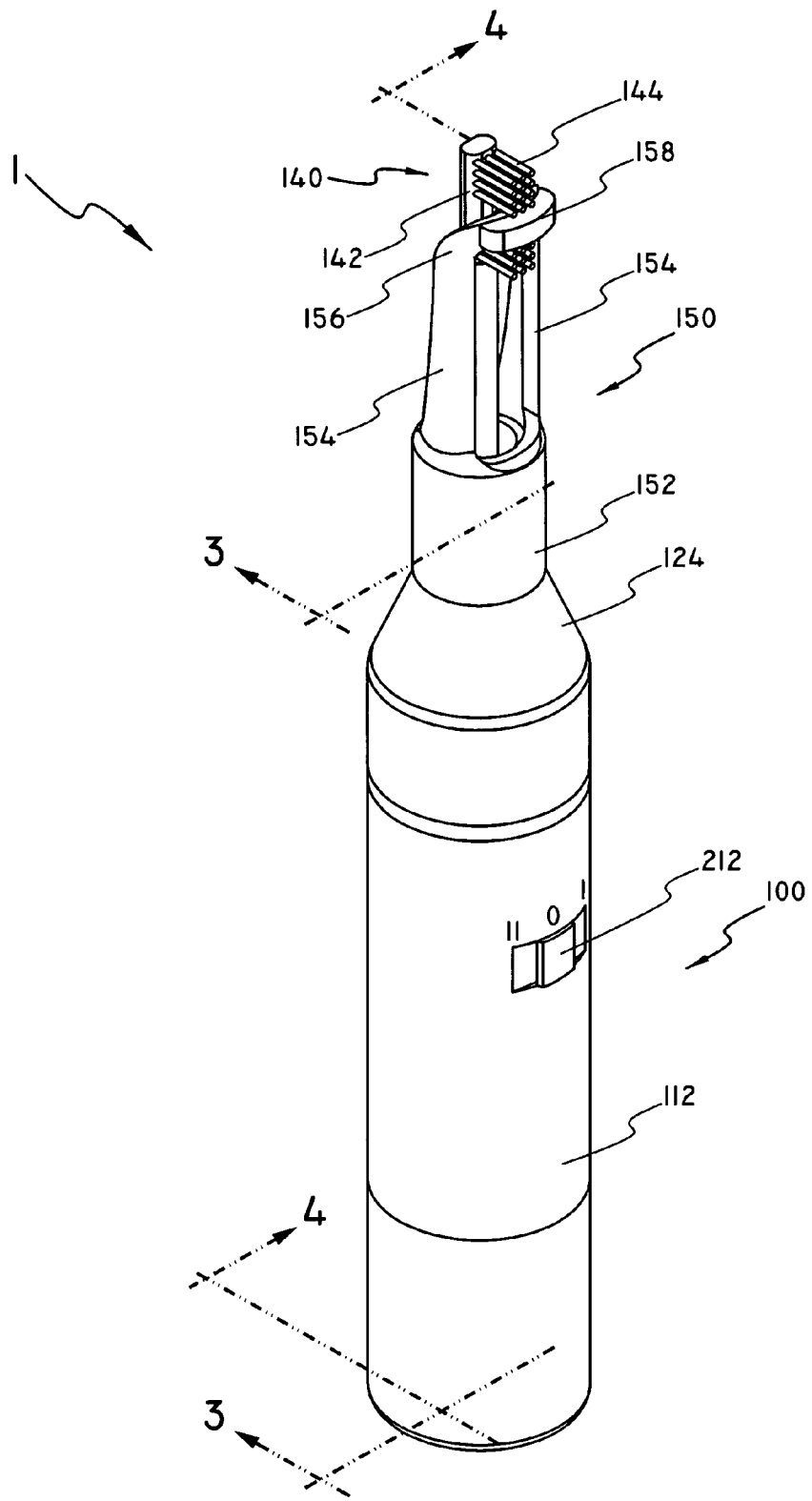
FIG. 1 is a perspective view of the toothbrush of the present invention.
Figure 2:
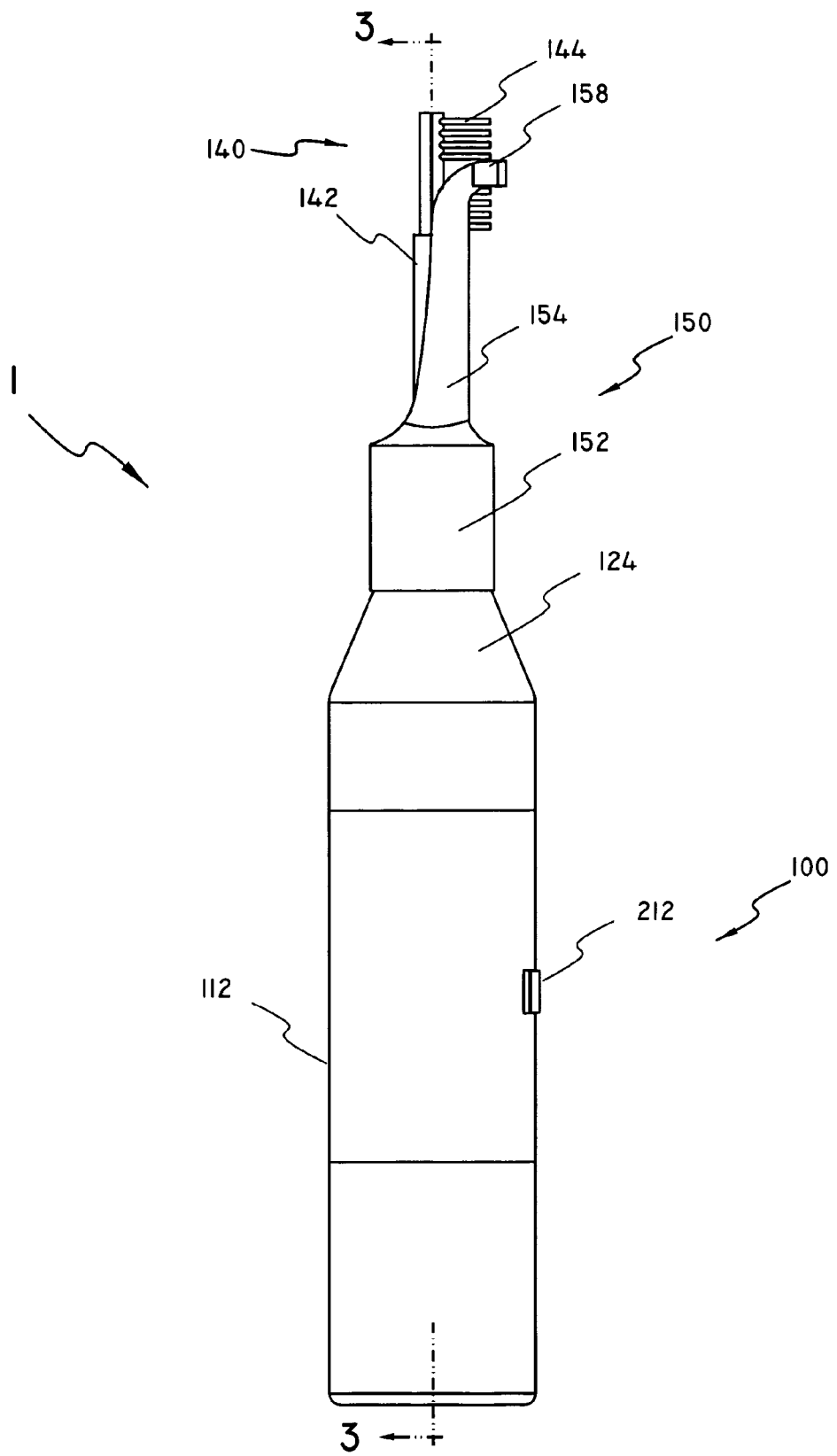
FIG. 2 is a side view of the toothbrush of the present invention.

The toothbrush 1, generally presented at FIGS. 1 and 2, includes a handle 100 and a brush head 140. Handle 100 is further composed of a body housing 112 and shoulder housing 124, while brush head 140 is further composed of brush shaft 142 and bristles 144. A switch 212 controlling the a motor 200 (FIG. 5) located within the body housing 112 is located on the body housing 112. The body housing 112 is substantially cylindrical in shape, having a closed lower end and an open upper end. It would be evident to one of ordinary skill in the art, however, that the body housing 112 may take any one of a variety of other shapes without departing from the spirit of the invention. The shoulder housing 124 is substantially frustoconical in shape having a larger, open lower end adapted to mate with the open upper end of the body housing 112 and a substantially closed upper end with an aperture centered therein allowing the passage of a brush drive shaft (to be detailed herein below).

Still referring to FIGS. 1 through 4, a brush spacer unit 150 extends upwardly from the top of the shoulder housing 124. The brush spacer unit 150 consists of a substantially cylindrical brush spacer base 152, which extends from the top of the shoulder housing 124, and a pair of brush spacer extenders 154, extending from the top of the brush spacer base 152, one on each side of the brush shaft 142. At a distal end, the brush spacer extenders 154 are joined by a brush spacer bridge 156, which passes in front of the brush shaft 142, through a gap in the bristles 144. The brush spacer bridge 156 is faced by a brush spacer pad 158.

Figure 3:
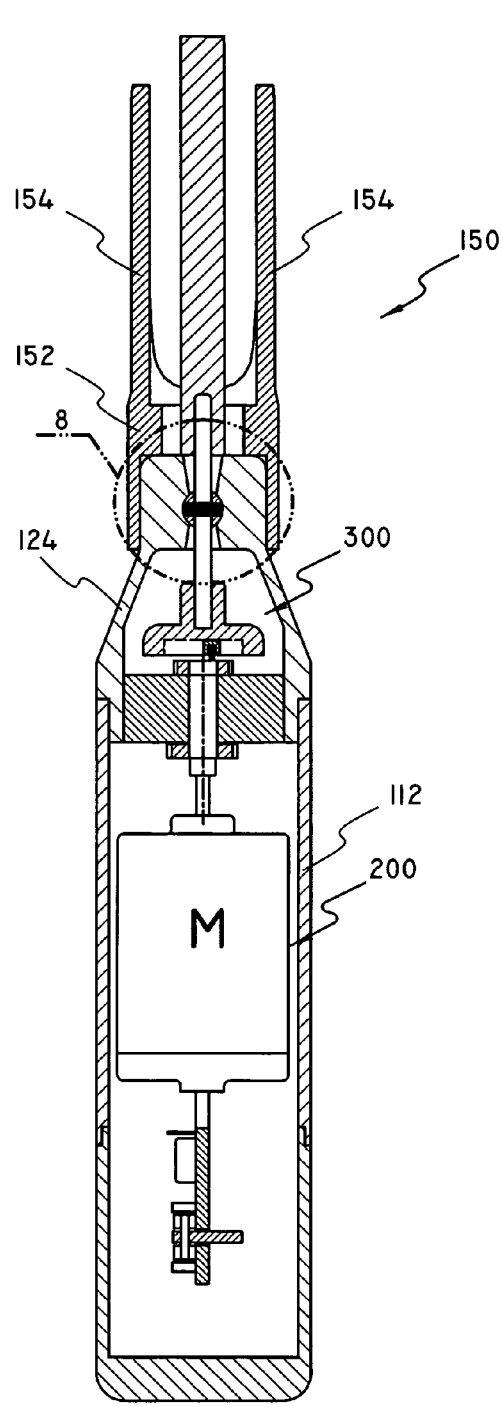
FIG. 3 is a cross sectional view of the toothbrush of the present invention as shown at line 3-3 of FIGS. 1 and 2.
Figure 4:
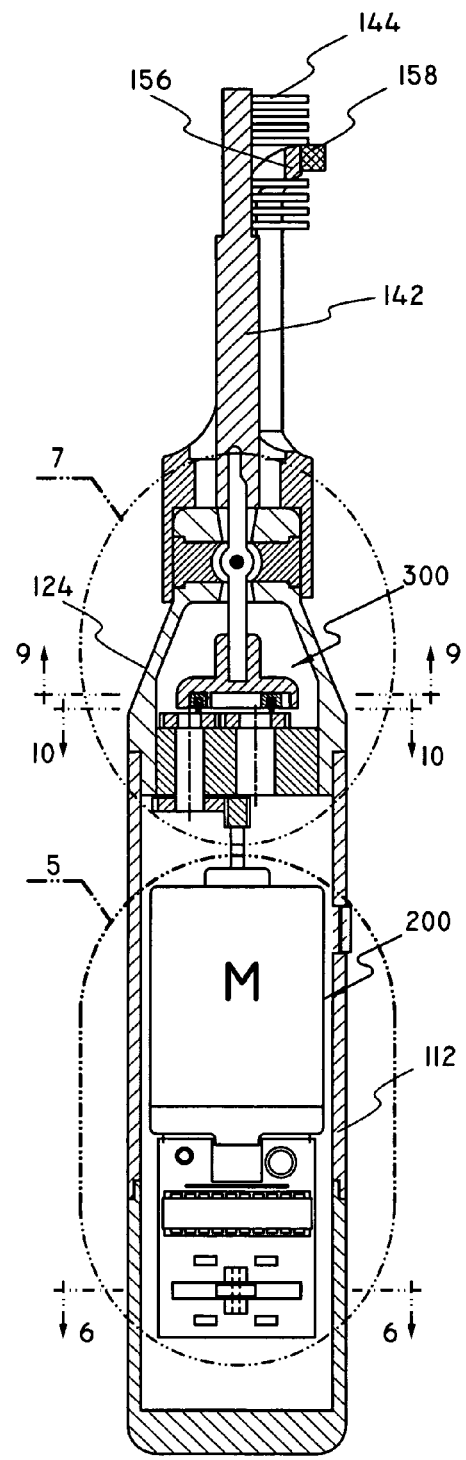
FIG. 4 is a cross sectional view of the toothbrush of the present invention as shown at line 4-4 of FIG. 1.

FIGS. 3 and 4 are front and side cross sectional views, respectively, showing the motor assembly 200 and elliptical rotation mechanism 300 as they are mounted within the body housing 112 and shoulder housing 124, the details of which will be discussed hereinbelow.

Figure 5:
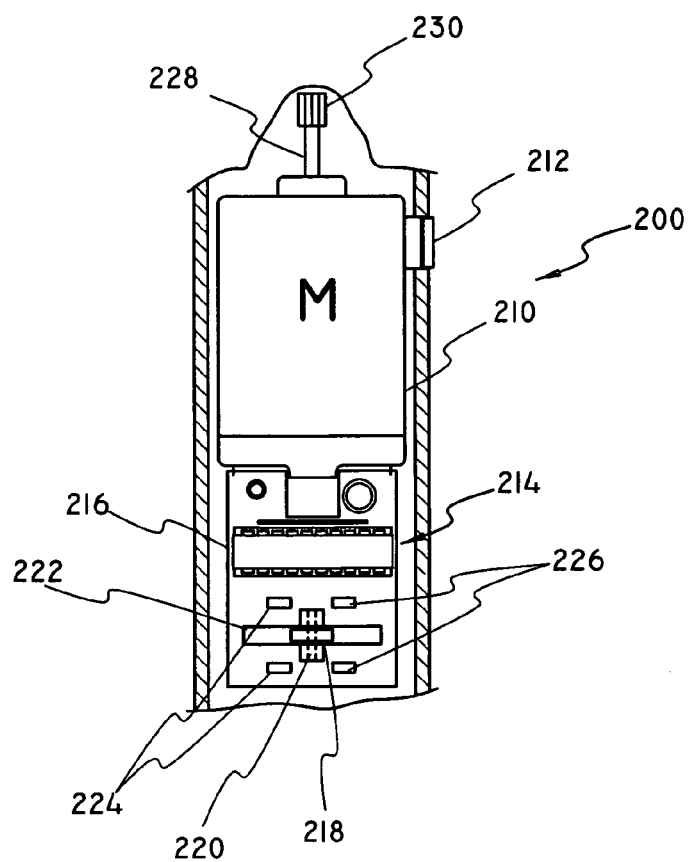
FIG. 5 is a detailed view of the electric motor, electronic control board and direction control mechanism, as isolated at 5 of FIG. 4.
Figure 6:
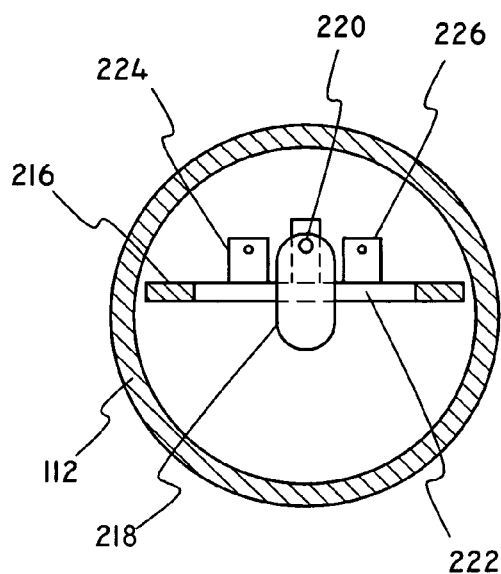
FIG. 6 is a detailed cross sectional view of the electric motor assembly of the toothbrush at line 6-6 of FIG. 4.

Turning now to FIGS. 5 and 6, the motor assembly 200 contains a reversible electric motor 210 which is powered by an electrical energy source (not shown) which could be either an AC power cord attached to a power grid, or a DC battery contained within the body housing 112. In the interest of safety and convenience, a DC battery (not shown) is the preferred power source, whether replaceable or rechargeable. The electric motor 210 is controlled by a three position switch 212 which passes through the wall of the body housing 112. The three positions of the switch 212 consist of "off", and a pair of reversing positions, which are selectively used for brushing the upper or the lower teeth. The electric motor 210 is further controlled by a directional controller 214 which allows the electric motor 210 to automatically reverse its direction of rotation. The directional control 214 consists of an electronic control board 216 and a pendulum 218 suspended from a pivot point 220 within a slot 222 in the electric control board 216. A pair of infra-red (IR) transceivers 224 and 226 are situated to the right and left, respectively, of the pendulum 218, such that the two elements of each transceiver 224 and 226 are on opposite sides of the slot 222. As the user of the toothbrush 1 changes the angle of the brush in his hand, pendulum 218 swings between the two elements of either transceiver 224 or 226, interrupting the infra-red beam. The interruption of the IR beam causes electronic control board 216 to reverse the direction of rotation of motor drive shaft 228 and drive gear 230, thus reversing the direction of rotation of the brush head 140. After the three position switch 212 is set for either the upper or lower teeth, the directional controller 214 reverses the direction of the electric motor 210 as the angle of the toothbrush 1 changes shifting from the right to left teeth, or front and back of the teeth. It would be evident to one of ordinary skill in the art that a variety of different position sensitive switching mechanisms known in the art, such as, but not limited to, a mercury switch, could be used in lieu of pendulum 218 and IR transceivers 224 and 226, without departing from the spirit of the present invention.

At FIGS. 7, 8, 9 and 10 the elliptical drive mechanism 300, which converts the rotary motion of the motor drive shaft 228 to an elliptical motion of the brush head 140, is illustrated. The elliptical drive mechanism 300 has a body block 310 which engages the interior of the lower end of the shoulder housing 124 such that drive gear 230 at the end of motor drive shaft 228 engages lower gear 312, which is fixedly attached, concentrically, to the lower end of gear shaft 314, which passes upwardly through body block 310. Upper gear 316 is fixedly attached, concentrically, to the upper end of gear shaft 314. A metal pin 318, having a ball head at its upper end, is fixedly attached, eccentrically and normal to the upper surface of upper gear 316. Upper gear 316 engages gear 320, which is rotatably and concentrically attached to a gear shaft 322, fixedly embedded in body block 310. A second metal pin 324, also having a ball head, is fixedly attached, eccentrically and normal to the upper surface of gear 320. The ball head of each of pin 318 and 324 are movably fitted into a cylindrical opening in the bottom of a cube-shaped drive cap 326, 328, respectively.

Figure 7:
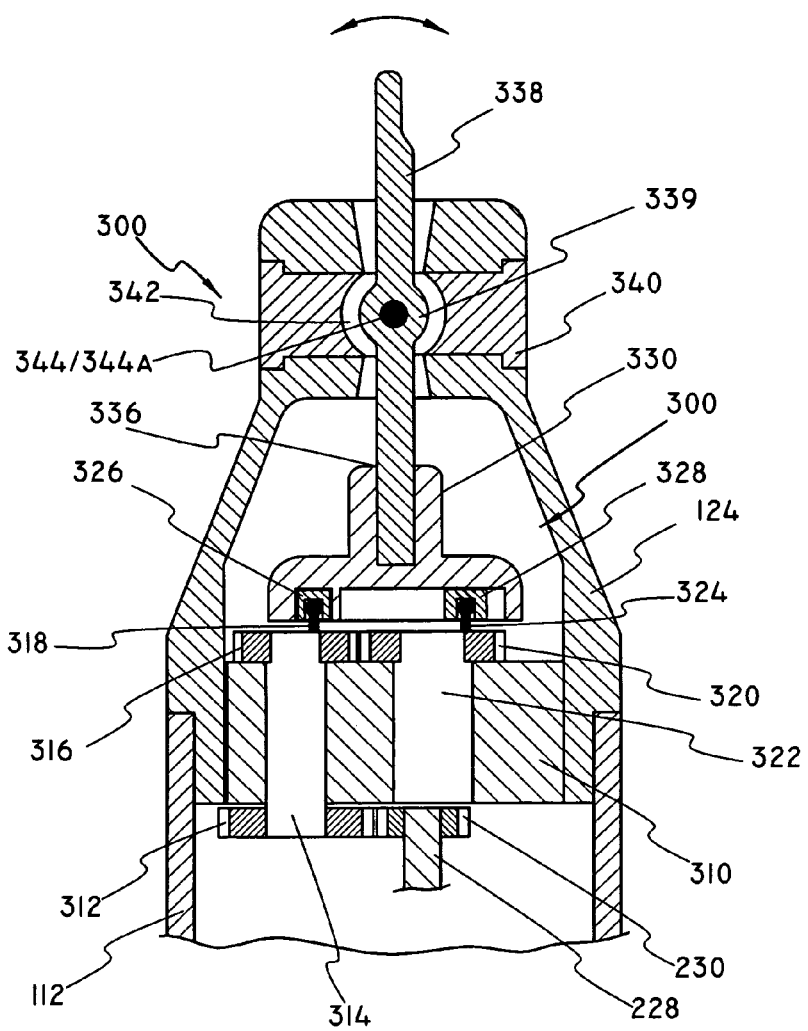
FIG. 7 is a detailed cross sectional view of the joint and elliptical rotation mechanism at line 4-4 of FIG. 1 as isolated at 7 of FIG. 4.
Figure 9:
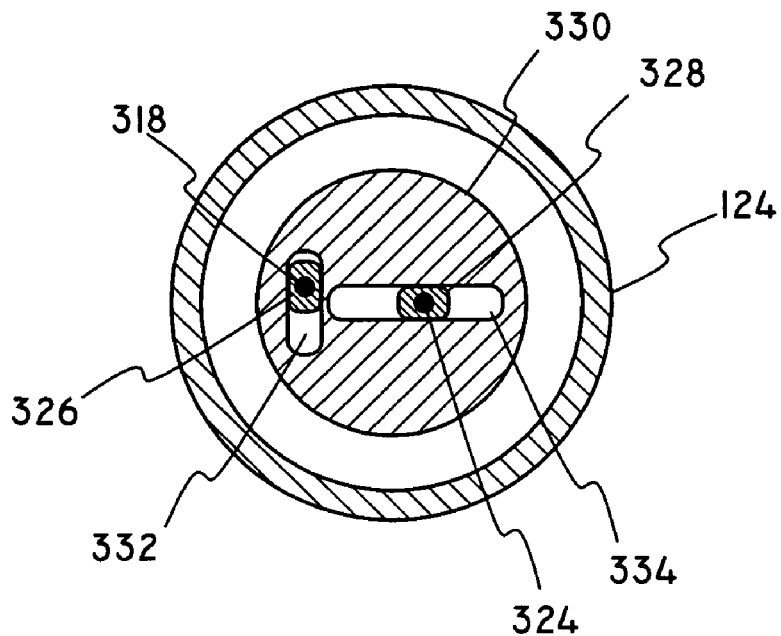
FIG. 9 is a cross sectional view of the elliptical rotation mechanism at line 9-9 of FIG. 4.
Figure 10:
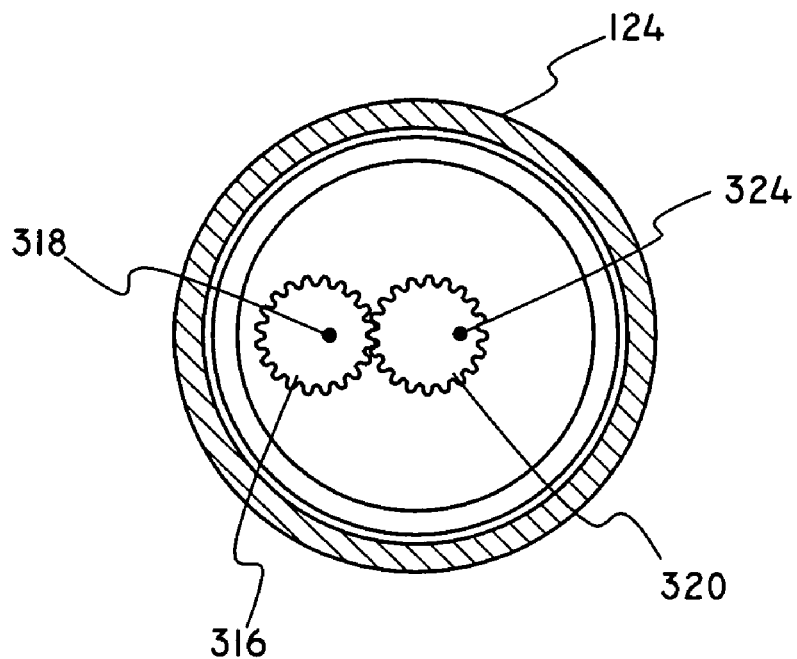
FIG. 10 is a cross sectional view of the elliptical rotation mechanism at line 10-10 of FIG. 4.
Figure 11:
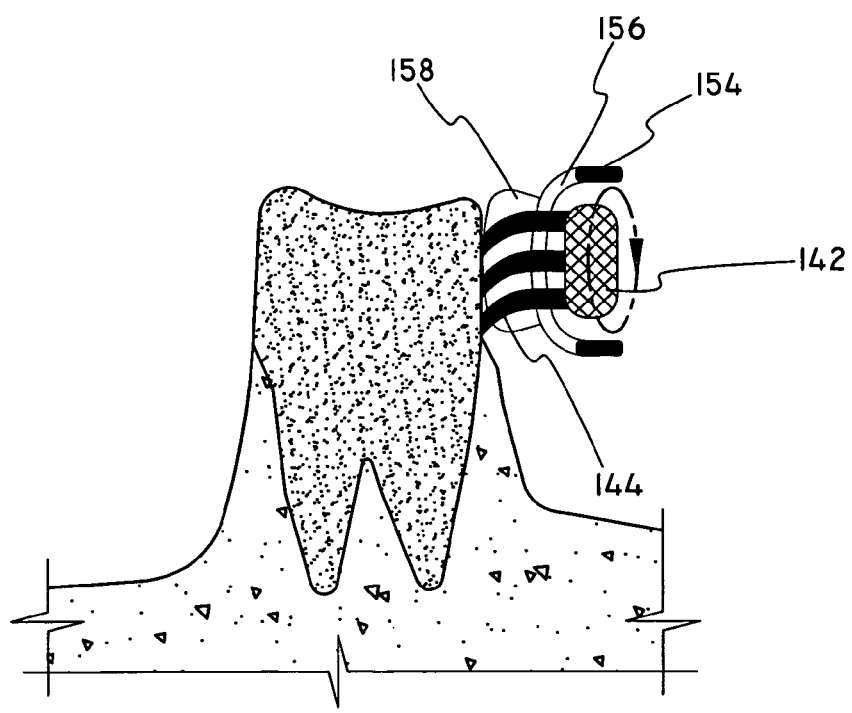
FIG. 11 is a view of the brush head of the tooth brush of the present invention brushing a lower tooth with the bristles at the brushing stroke position of the brush drive shaft's elliptical cycle.
Figure 12:
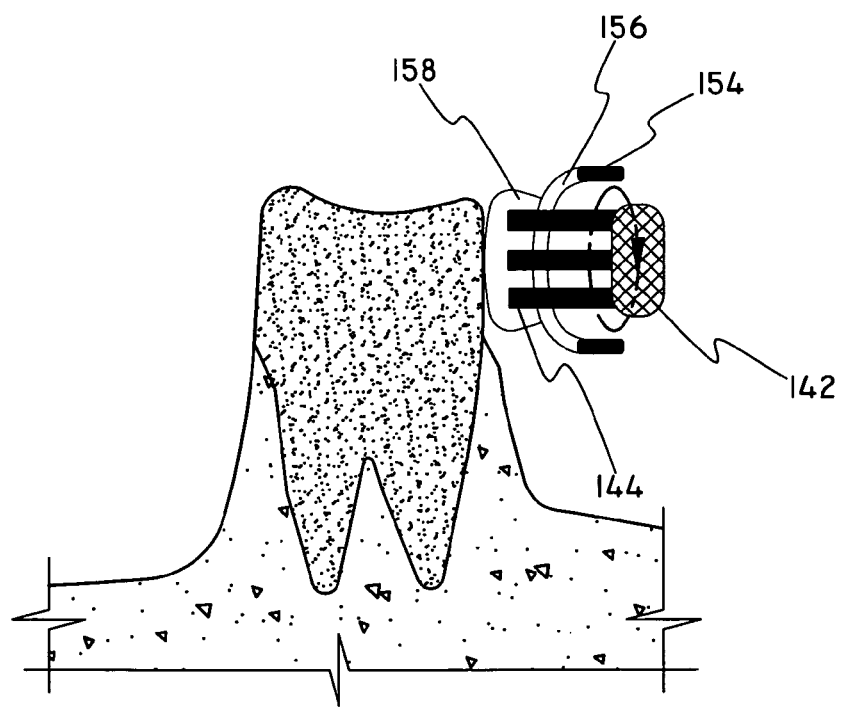
FIG. 12 is a view of the brush head of the tooth brush of the present invention and a lower tooth with the bristles at the recovery portion of the brush drive shaft's elliptical cycle.
Figure 13:
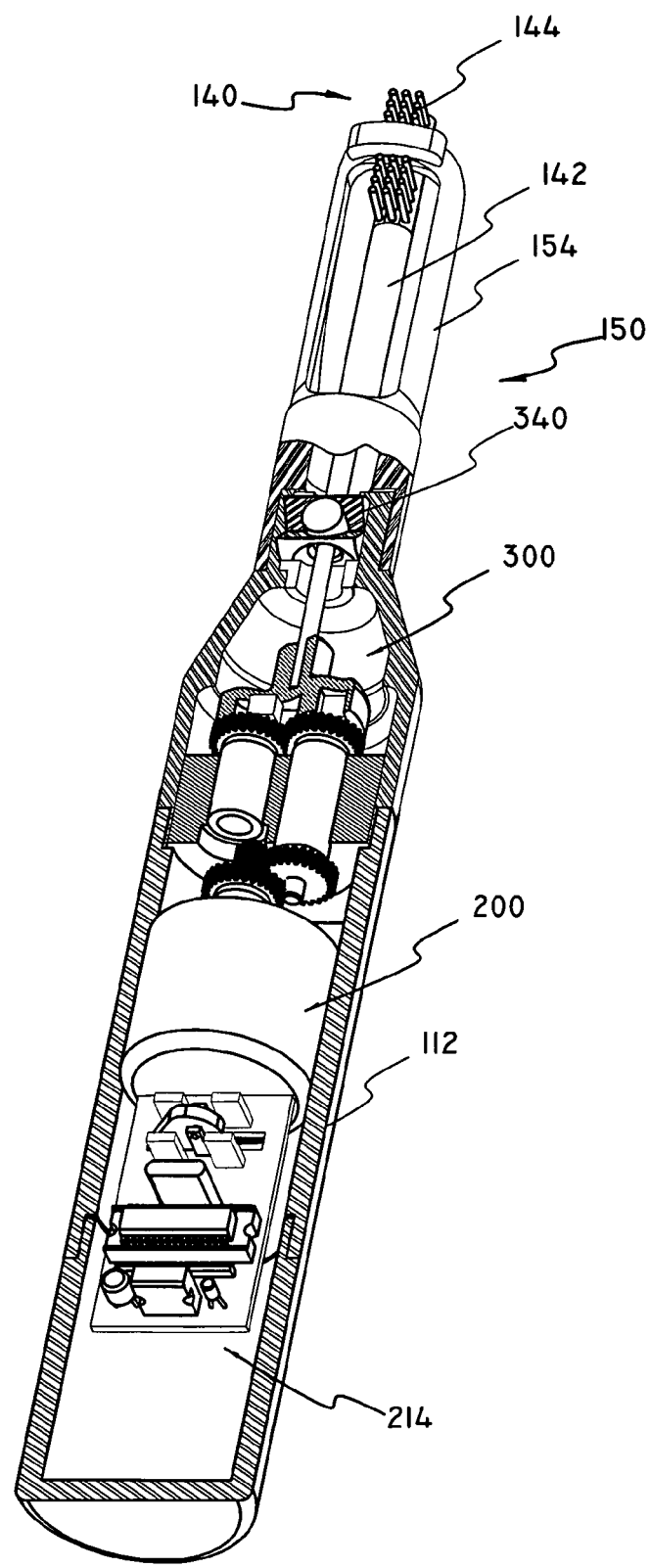
FIG. 13 is a partially cut away perspective view of the toothbrush showing the operating systems with additional detail.
Figure 14:
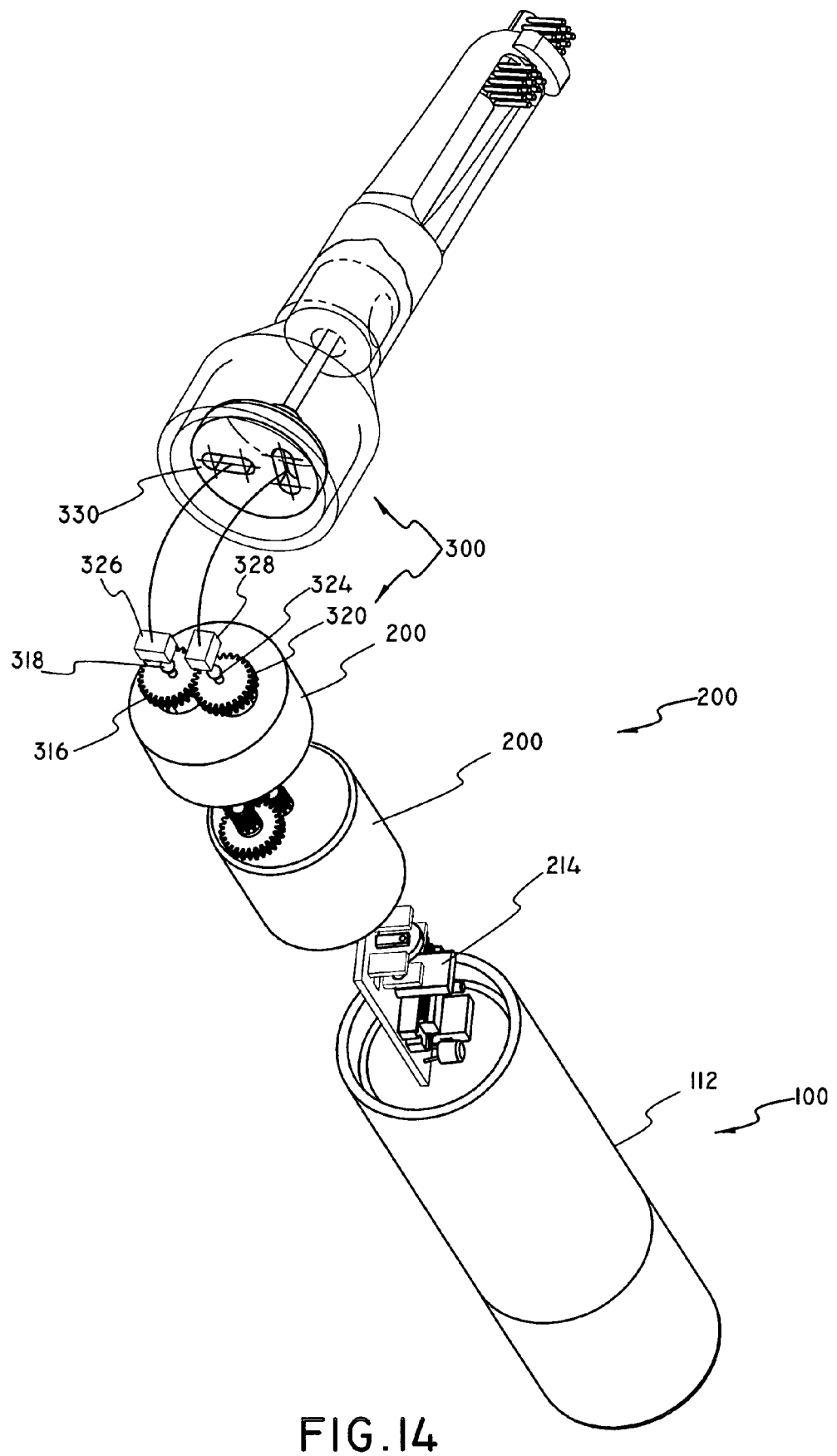
FIG. 14 an exploded perspective view of the toothbrush showing the interlinking of the operating mechanisms between the various segments of the assembly.

Still referring to FIGS. 7 and 9, an elliptical drive head 330 is of a diameter sufficiently smaller than the interior diameter of shoulder housing 124 (FIG. 2) to allow free movement within shoulder housing 124. Within the lower surface of elliptical drive head 330 are a groove 332 and a groove 334, adapted to movably receive drive caps 326 and 328, respectively.

Groove 332 is located in the lower surface of elliptical drive head 330 near its circumference. It is normal to and centered on a diameter line of elliptical drive head 330. Groove 334, also on the lower surface of elliptical drive head 330, lies along the aforementioned diameter line bisecting, but not joining groove 332 and is disposed such that a first end is proximate groove 332 and a second end is proximate the circumference of elliptical drive head 330. The second end of groove 334 is approximately equidistant from the circumference of elliptical drive head 330 as is the outer edge of groove 332. Within the upper surface of elliptical drive head 330 is a cylindrical drive shaft receptacle 336, adapted to frictionally receive the lower end of brush drive shaft 338.

Drive caps 326, 328 each fit into the grooves 332 and 334, respectively, such that as the gears 316 and 320 turn, thereby moving the drive caps 326, 328 within the grooves 332 and 334, elliptical drive head 330 moves eccentrically within the shoulder housing 124, thereby causing the lower end of the brush drive shaft 338 to move eccentrically. The eccentric motion of the lower end of the brush drive shaft 338 is transferred to the upper end and thus the bristles, 144 by the pivot assembly 340, further detailed hereinbelow.

Brush drive shaft 338 is substantially a parallelepiped having a length substantially greater than its substantially square cross section. A rounded protrusion 339 may be located in two of the opposite faces of the length of brush drive shaft 338 proximate its center point provide additional space for a round pivot pin 344 and pivot pin aperture 344A which penetrates brush drive shaft 338 proximate its midpoint, passing between the flat faces of brush drive shaft 338.

Figure 8:
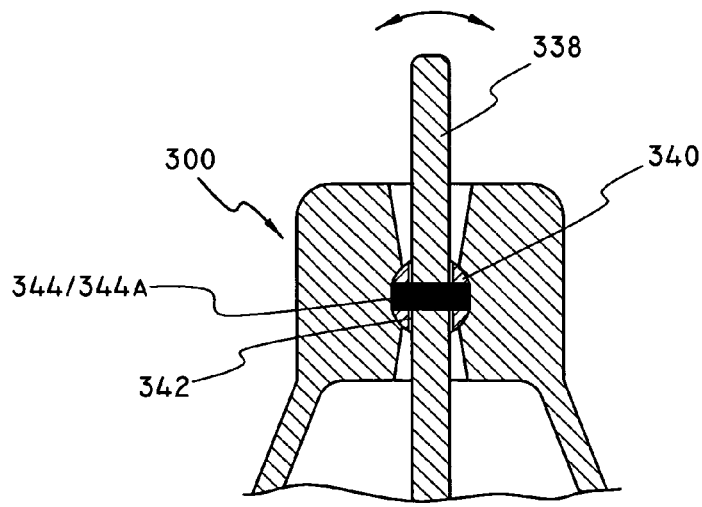
FIG. 8 is a detailed cross sectional view of the joint of the elliptical rotation mechanism at line 3-3 of FIG. 1.

Referring now to FIGS. 7 and 8, there is shown a pivot assembly 340 which occupies a void within shoulder housing 124. The pivot assembly 340 is composed of a substantially solid and rectilinear bar dimensioned so that its ends frictionally engage the interior walls of shoulder housing 124. A pivot aperture 342 within pivot assembly 340 allows brush drive shaft 338 to pass vertically therethrough. A pivot pin 344 passing through pivot pin aperture 344A of brush drive shaft 338 is anchored at each of its two ends into the interior walls of pivot assembly 340, movably securing brush drive shaft 338 within pivot assembly 340.

It would be evident to one of ordinary skill in the art that various bushings and bearings would be required to facilitate the smooth working of gears and pivot points. These bushing and bearings are well known in the art, therefore they will not be discussed in further detail herein. It would, likewise, be evident to one of ordinary skill in the art that toothbrush 1 could be manufactured of a variety of different materials, but for the sake of economy, various polymerics or plastics would be preferable for housings, shafts and gears, although light metals could also be utilized.

In operation, switch 212 activates electric motor 210 in one of either a clockwise or counter-clockwise direction, the direction depending on the initial position of pendulum 218. The user, by rotating his wrist, and thereby toothbrush 1, causes pendulum 218 of directional control 214 to swing in a direction corresponding to the rotation of the wrist. As pendulum 218 breaks the IR beam of either IR transceiver 224 or 226, directional controller 216 is caused to reverse the direction of motor drive shaft 228 of motor 210. Drive gear 230, mounted at the end of motor drive shaft 228, being rotatably engaged with lower gear 312 causes lower gear 312 to drive gear shaft 314, and thus, upper gear 316. Upper gear 316, in turn, drives gear 320, respectively causing elliptical drive head 338 to move elliptically. It will be noted that neither elliptical drive head 330 nor brush drive shaft 338 rotate, but rather, keep a constant orientation in a single direction. Brush drive shaft 338, pivoting about pivot pin 344, transfers the elliptical motion to brush shaft 142 of brush head 14, and thus to the bristles 144 of brush head 14. Again, by twisting the wrist, the user may reverse the direction of elliptical rotation of brush head 14 so that the bristles 114 may travel downwardly for brushing the upper teeth or upwardly for brushing the lower teeth, as is typically recommended by most dental professionals.

Figure 15:
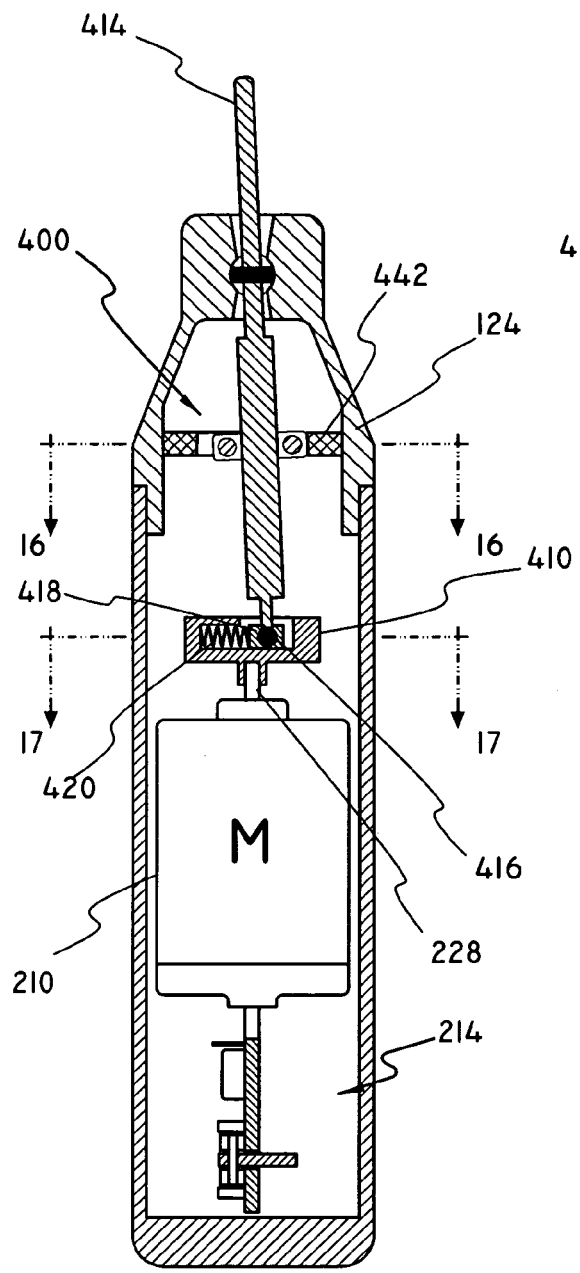
FIG. 15 is a cut away view of an alternative embodiment of the toothbrush having an alternative elliptical rotation mechanism.
Figure 16:
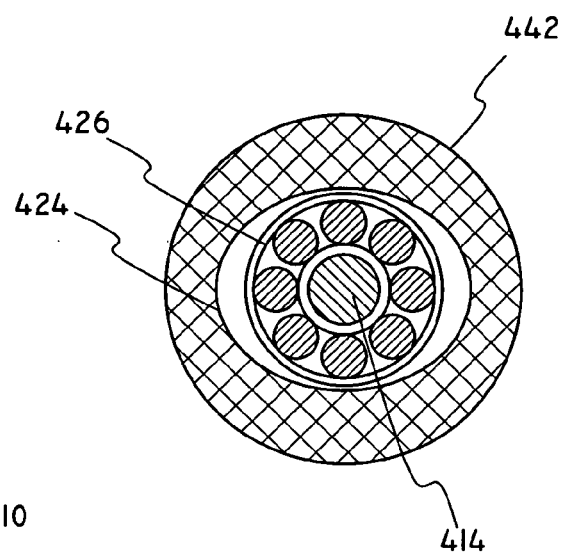
FIG. 16 is a cross sectional view of the alternative elliptical rotation mechanism at line 16-16 of FIG. 15.
Figure 17:
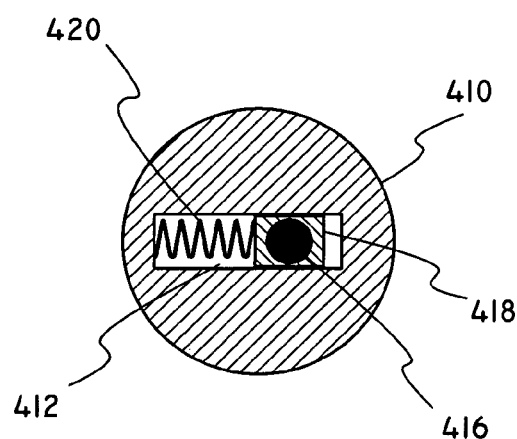
FIG. 17 is a cross sectional view of the alternative elliptical rotation mechanism at line 17-17 of FIG. 15.

Referring now to FIGS. 15, 16 and 17, an alternate embodiment of an elliptical drive mechanism 400 is presented. Instead of being gear driven, the elliptical drive mechanism is driven directly by electric motor 210. In the alternate embodiment 400, a motor drive shaft 228 terminates in the lower surface of a round drive plate 410, which has a groove 412 disposed in its upper surface. Brush drive shaft 414 has an elongate rectilinear form having a ball capped pin 416 at its lower end, the ball of which is movably secured in a cubic drive cap 418. A spring 420 moveably holds the cubic drive cap 418 eccentrically in position within the groove 412. The rotary motion of motor drive shaft 228 and drive plate 410 is converted to an elliptical motion of brush drive shaft 414 by the movable relationship of pin 416 and drive cap 418, as well as the movable relationship of drive cap 418 within groove 412. A round guide plate 442 is adapted to fit frictionally within the inner walls of shoulder housing 124. Guide plate 442 has an elliptical aperture 424 at its center, which houses a roller bearing assembly 426, which in turn surrounds an end of brush drive shaft 414. Pivot assembly 340 of the preferred embodiment remains, unchanged, in the alternate embodiment. The combined actions of the eccentricity of the end of brush drive shaft 414 in drive plate 410, the elliptical aperture in guide plate 442 and the fixed pivot point of pivot assembly 340 provide the elliptical motion to brush head 14.

It is to be understood that the present invention is not limited to the embodiments described above, but encompasses any and all embodiments within the scope of the following claims.

What is claimed is:

1. An electric toothbrush comprising:
   housing means for giving said toothbrush form, said housing means comprising an elongate, substantially hollow handle portion and a substantially hollow shoulder portion, said housing means supporting the following working elements of said toothbrush:
   brushing means for brushing a user's teeth,
   spacing means for spacing said brushing means away from the surface of a user's teeth, said spacing means comprising:
      a pair of brush spacer extenders extending from said shoulder portion, each of said brush spacer extenders being substantially opposite the other of said brush spacer extenders,
      a brush spacer bridge extending between a distal end of said pair of brush spacer extenders, and a brush spacer pad affixed to said brush spacer bridge, said brush spacer pad adapted to interface with the surface of a user's teeth,
   power means for providing power to said toothbrush,
   motor means for converting said power into rotary motion of a drive shaft of said motor means,
   switch means for turning said motor means on and off and controlling the direction of rotation of the drive shaft of said motor means as determined by the teeth to be brushed, from among the group consisting of the upper teeth and the lower teeth, and
   conversion means for converting the rotary motion of said motor means drive shaft to an elliptical motion of said brushing means.

2. An electric toothbrush, as defined in claim 1, wherein said brushing means comprises:
   a brush shaft and
   a bristled head, said bristles being formed along one face of said brush shaft, a gap being formed in said bristles such that said brush spacer bridge may lay between said bristles.

3. An electric toothbrush, as defined in claim 2, wherein said motor means comprises a reversible electric motor housed within said substantially hollow handle portion of said housing means, said motor means drive shaft centered on and running parallel to the length of said housing means.

4. An electric toothbrush, as defined in claim 3, wherein said drive shaft terminates in a drive gear.

5. An electric toothbrush, as defined in claim 3, wherein said switch means comprises a three position switch, said three positions comprising off, forward and reverse.

6. An electric toothbrush, as defined in claim 5, wherein said switch further comprises a position sensitive switch which automatically reverses said direction of rotation of said drive shaft based on the angle at which said toothbrush is held in a user's hand after said initial direction of rotation has been established by the position of the three position switch.

7. An electric toothbrush, as defined in claim 6, wherein said position sensitive switch further comprises a pendulum and two pairs of infra-red (IR) sensors, wherein said pendulum is free to move between the two elements of each of said two pairs of IR sensors, said pendulum interrupting the signal between one or the other of said pair of IR sensors, the direction of rotation of said motor being reversible depending on which of said two pairs of IR sensors said pendulum has interrupted, said pendulum being activated by changes in the positioning of a user's hand.

8. An electric toothbrush, as defined in claim 7, wherein said conversion means comprises an elliptical drive mechanism, said elliptical drive mechanism comprising:
   a substantially round drive plate having:
      an aperture formed in a lower surface thereof, said aperture adapted to concentrically receive an end of said drive shaft of said motor means, and a groove disposed in an upper surface thereof, said groove lying along a diametric line of said round drive plate,
      a drive cap dimensioned and configured to movably fit within said groove, said drive cap having an aperture formed in an upper surface thereof,
      a spring dimensioned and configured to fit within a first end of said groove such that it exerts pressure against one side of said drive cap, thereby forcing said drive cap to the second end of said groove when said spring is in a relaxed state, and
   a substantially round guide plate comprising:
      a substantially elliptical aperture formed concentrically therethrough,
      a substantially round roller bearing assembly mounted within said substantially elliptical aperture, said roller bearing assembly having an aperture formed through the center thereof,
   a pivot assembly having an aperture formed therethrough, said pivot assembly located within an upper portion of said shoulder portion, positioned at a distance above said guide plate, and
   a brush drive shaft, said brush drive shaft having a length with a first end movably constrained within said drive cap within said drive plate, said length of said brush drive shaft movably passing through said aperture in said roller bearing assembly and said pivot assembly aperture, and a second end extending beyond said pivot assembly.

9. An electric toothbrush, as defined in claim 8, wherein said lower portion of said brush shaft is substantially hollow, said hollow portion receiving said second end of said brush drive shaft therein.

10. An electric toothbrush, as defined in claim 2, wherein said conversion means comprises an elliptical drive mechanism, said elliptical drive mechanism comprising:
   a body block, said body block adapted to fit snugly within said substantially hollow shoulder portion of said housing means, said body block further comprising:
      a first lower gear fixedly mounted at the lower end of a first gear shall rotatably penetrating said body block and a first upper gear fixedly mounted at the upper end of said first gear shaft,
      a second upper gear rotatably mounted the upper end of a second gear shaft fixedly mounted in the upper surface of said body block, said first upper gear engaging said second upper gear,
      a first metal pin having a substantially ball-shaped head extending eccentrically from and normal to the upper surface of said first upper gear,
      a second metal pin having a substantially ball-shaped head extending eccentrically from and normal to the upper surface of said second upper gear,
      two drive caps movably mounted respectively over said ball-shaped head of each of said first and second metal pin,
   a substantially round elliptical drive head having a diameter sufficiently smaller than the interior of said shoulder portion to allow free movement within said shoulder housing, said elliptical drive head further comprising:
      a first groove formed in a lower surface of said elliptical drive head, said first groove having a length and a width sufficiently larger than said drive caps to allow movement of said drive cap of said first pin to easily move along said length of said groove, said first groove lying along a portion of a diameter line of said lower surface of said elliptical drive head, and
      a second groove formed in said lower surface of said elliptical drive head, said second groove having a length and a width sufficiently larger than said drive caps to allow movement of said drive cap of said second pin to easily move along said length of said second groove lying normal to and being bisected by an extension of said radial line, the ends of said second groove being proximate the perimeter of said lower surface of said elliptical drive head,
      a substantially round aperture formed in the upper surface of said elliptical drive head, said aperture being adapted to receive a first end of a brush drive shaft,
      a pivot assembly having an aperture formed therethrough, said pivot assembly being frictionally held within an upper portion of said shoulder portion, at a distance above said elliptical drive head, and
      a brush drive shaft, said brush drive shaft being substantially a parallelapiped having a first end moveably constrained within said aperture formed in said upper surface of said elliptical drive head, a mid-portion movably constrained within said pivot assembly aperture, and a second end extending beyond said pivot assembly.

11. An electric toothbrush, as defined in claim 10, wherein said lower portion of said brush shaft is substantially hollow, said hollow portion receiving said second end of said brush drive shaft therein.

12. An electric toothbrush, as defined in claim 1, wherein said switch means comprises a three position switch, said three positions comprising off, forward, and reverse.

13. An electric toothbrush, as defined in claim 12, wherein said switch further comprises a position sensitive switch which automatically reverses said direction of rotation of said drive shaft based on the angle at which said toothbrush is held in a user's hand after said initial direction of rotation has been established.

14. An electric toothbrush comprising:

housing means for giving said toothbrush form and supporting the following working elements of said toothbrush:
- brushing means for brushing a user's teeth,
- spacing means for spacing said brushing means away from the surface of a user's teeth,
- power means for providing power to said toothbrush,
- motor means for converting said power into rotary motion of a drive shaft of said motor means,
- switch means for turning said motor means on and off and controlling the direction of rotation of the drive shaft of said motor means as determined by the teeth to be brushed, from among the group consisting of the upper teeth and the lower teeth, and
- conversion means for converting the rotary motion of said motor means drive shaft to an elliptical motion of said brushing means, wherein said switch further comprises a position sensitive switch which automatically reverses said direction of rotation of said drive shaft based on the angle at which said toothbrush is held in a user's hand after said initial direction of rotation has been established, and wherein said position sensitive switch further comprises a pendulum and two pairs of infra-red (IR) sensors, wherein said pendulum is free to move between the two elements of each of said two pairs of IR sensors, said pendulum interrupting the signal between one or the other of said pair of IR sensors, the direction of rotation of said motor being reversible depending on which of said two pairs of IR sensors said pendulum has interrupted, said pendulum being activated by changes in the positioning of a user's hand.

15. An electric toothbrush comprising:

housing means for giving said toothbrush form, said housing means comprising an elongate, substantially hollow handle portion and having at an upper end thereof a substantially hollow shoulder portion, said housing means supporting the following working elements of said toothbrush:
- brushing means for brushing a user's teeth,
- spacing means for spacing said brushing means away from the surface of a use's teeth,
- power means for providing power to said toothbrush,
- motor means for converting said power into rotary motion of a drive shaft of said motor means,
- switch means for turning said motor means on and off and controlling the direction of rotation of the drive shaft of said motor means as determined by the teeth to be brushed, from among the group consisting of the upper teeth and the lower teeth, and
- conversion means for converting the rotary motion of said motor means drive shaft to an elliptical motion of said brushing means, wherein said conversion means comprises an elliptical drive mechanism, said elliptical drive mechanism comprising:

a substantially round drive plate having:
- an aperture formed in a lower surface thereof, said aperture adapted to concentrically receive an end of said drive shaft of said motor means, and a groove disposed in an upper surface thereof, said groove lying along a diametric line of said round drive plate,
- a drive cap dimensioned and configured to movably fit within said groove, said drive cap having an aperture formed in an upper surface thereof,
- a spring dimensioned and configured to fit within a first end of said groove such that it exerts pressure against one side of said drive cap, thereby forcing said drive cap to the second end of said groove when said spring is in a relaxed state, and a substantially round guide plate comprising:
- a substantially elliptical aperture formed concentrically therethrough,
- a substantially round roller bearing assembly mounted within said substantially elliptical aperture, said roller bearing assembly having an aperture formed through the center thereof, a pivot assembly having an aperture formed therethrough, said pivot assembly being located within an upper portion of said shoulder portion, positioned at a distance above said guide plate, and a brush drive shaft, said brush drive shaft having a length width a first end movably constrained within said drive cap within said drive plate, said length of said brush drive shaft movably passing through said aperture in said roller bearing assembly and said pivot assembly aperture, and a second end extending beyond said pivot assembly.

* * * * *